United States Patent
Chiu et al.

(10) Patent No.: US 7,759,710 B1
(45) Date of Patent: Jul. 20, 2010

(54) OXIDIZED LOW DENSITY LIPOPROTEIN SENSING DEVICE FOR GALLIUM NITRIDE PROCESS

(75) Inventors: Hsien-Chin Chiu, Taipei (TW); Chao-Sung Lai, Taoyuan (TW); Bing-Shan Hong, Banqiao (TW); Chao-Wei Lin, Fengyuan (TW); S. E. Chow, Taipei (TW); Ray-Ming Lin, Xinzhuang (TW); Yung-Hsiang Lin, Taipei (TW); Hsin-Shun Huang, Xinzhuang (TW)

(73) Assignee: Chang Gung University, Taoyuan County (TW)

( * ) Notice: Subject to any disclaimer, the term of this patent is extended or adjusted under 35 U.S.C. 154(b) by 0 days.

(21) Appl. No.: 12/435,457

(22) Filed: May 5, 2009

(51) Int. Cl.
*H01L 29/778* (2006.01)
(52) U.S. Cl. ................. 257/253; 257/E29.166
(58) Field of Classification Search .......... 257/253
See application file for complete search history.

(56) References Cited

U.S. PATENT DOCUMENTS

| | | | |
|---|---|---|---|
| 5,200,051 A * | 4/1993 | Cozzette et al. | 204/403.07 |
| 6,914,279 B2 * | 7/2005 | Lu et al. | 506/39 |
| 7,382,004 B2 * | 6/2008 | Shur et al. | 257/253 |
| 7,394,118 B2 * | 7/2008 | Zhou | 257/253 |
| 2007/0086915 A1 * | 4/2007 | LeBoeuf et al. | 422/58 |
| 2008/0308846 A1 * | 12/2008 | Shim et al. | 257/253 |
| 2009/0152596 A1 * | 6/2009 | Yang et al. | 257/253 |
| 2009/0321792 A1 * | 12/2009 | Chou et al. | 257/253 |

* cited by examiner

*Primary Examiner*—Evan Pert (57) ABSTRACT

An oxidized low density lipoprotein sensing device for a gallium nitride process is a GaN HEMT device including: a gateless AlGaN/GaN sensing transistor device, a testing window, a source, a drain, two metal connecting wires and a passivation layer. The gateless AlGaN/GaN sensing transistor device has an epitaxial wafer structure including a GaN layer and an aluminum gallium nitride layer. The testing window is disposed on the epitaxial wafer structure. The metal connecting wire is disposed on a source and a drain. The passivation layer is covered onto a surface of the sensing device except the testing window. A built-in piezoelectric field is created by the properties of FET and the polarization effect of AlGaN/GaN to achieve the effect of sensing the level of oxidizing proteins in human body quickly, accurately and easily.

9 Claims, 9 Drawing Sheets

OXIDIZED LOW DENSITY LIPOPROTEIN SENSING DEVICE FOR GALLIUM NITRIDE PROCESS

FIELD OF THE INVENTION

The present invention relates to a technical area of low density lipoprotein sensing devices, in particular to an oxidized low density lipoprotein sensing device for a gallium nitride process.

BACKGROUND OF THE INVENTION

Low density lipoprotein is an important substance for transporting cholesterols in human blood, and some of the transported low density lipoprotein cholesterols (LDL-cholesterols) are used by liver, and some are used by tissues and cells to produce cell walls and used for other purposes. If human blood contains too much low density lipoprotein cholesterol, the blood will be accumulated at coronary arteries of a heart or vessel walls of a brain to form lumps and narrow artery vessels. In other words, an atherosclerotic artery is resulted and cardiac muscles are perfused by a coronary artery blood flow or a cerebral blood flow, or the quantity of brain tissues is decreased to result in a cardiac muscle ischemia-hypoxia or a cerebral ischemia-hypoxia. If any lump at the vessel wall is cracked or broken, an acute thermobus formation will be induced to clog the whole blood vessel all of a sudden and obstruct the blood flow completely and cause symptoms of myocardial infarction or stroke. Since the low density lipoprotein cholesterol (LDL-cholesterol) with a high concentration is a major risk factor of heart diseases, the low density lipoprotein cholesterol is generally known as "bad" cholesterol.

A traditional medical examination usually adopts an electrophoresis to detect and measure the contents of low density lipoproteins and requires much time (such as eight hours) for the examination, and thus the traditional medical examination is not cost-effective and also has existing limitations and issues that require further improvements.

SUMMARY OF THE INVENTION

In view of the foregoing shortcomings of the prior art, the present invention provides an oxidized low density lipoprotein sensing device for a gallium nitride process, which is a GaN HEMT device, comprising: a gateless AlGaN/GaN sensing transistor device, a testing window, a source, a drain, two metal connecting wires, and a passivation layer, wherein the gateless AlGaN/GaN sensing transistor device is an epitaxial wafer structure, and the epitaxial wafer structure includes a GaN layer and an aluminum gallium nitride layer, and the aluminum gallium nitride layer is disposed on the GaN layer, and the aluminum gallium nitride layer includes aluminum of a certain weight percentage, and the aluminum gallium nitride layer comes with a certain thickness to achieve a lattice match. The testing window is disposed at the epitaxial wafer structure, wherein a source is disposed at the epitaxial wafer structure and on a side of the testing window, a drain is disposed at the epitaxial wafer structure and on another side of the testing window, and each metal connecting wire is installed separately on the source and the drain provided for the measurement. The passivation layer is covered onto the external surface of the gateless AlGaN/GaN sensing transistor device except the testing window for detecting the level of protein oxidation in human body quickly, accurately and easily.

Compared with the prior art, the present invention has the following advantages:

1. The present invention avoids complicated chemical testing methods and senses the level of protein oxidation in human body quickly, accurately and easily.

2. The present invention achieves the effects of a low cost, a high environmental resistance, and a low current leakage, etc.

DETAILED DESCRIPTION OF THE PREFERRED EMBODIMENTS

With reference to FIGS. 1 to 8, the present invention provides an oxidized low density lipoprotein sensing device for a gallium nitride process, which is a GaN high electron mobility transistor (HEMT) device 10, comprising: a gateless AlGaN/GaN sensing transistor device, a testing window 20, a source, a drain, two metal connecting wires and a passivation layer, wherein the gateless AlGaN/GaN sensing transistor device is an epitaxial wafer structure, and the epitaxial wafer structure includes a GaN layer 11 and an aluminum gallium nitride layer 12, and the aluminum gallium nitride layer 12 is disposed on the GaN layer 11, and the aluminum gallium nitride layer 12 includes aluminum of a certain weight percentage, and the aluminum gallium nitride layer 12 comes with a certain thickness to achieve a lattice match, and the testing window 20 is disposed at the epitaxial wafer structure, and the source is disposed at the epitaxial wafer structure and on a side of the testing window 20, and the drain is disposed at the epitaxial wafer structure and on another side of the testing window 20, and each metal connecting wire is disposed separately on the source and the drain, and the passivation layer is covered onto an external surface of the gateless AlGaN/GaN sensing transistor device except the testing window 20, such that a built-in piezoelectric field is created by the properties of FET and the polarization effect of AlGaN/GaN to achieve the effect of sensing the level of oxidizing proteins in human body quickly, accurately and easily.

Figure 4:
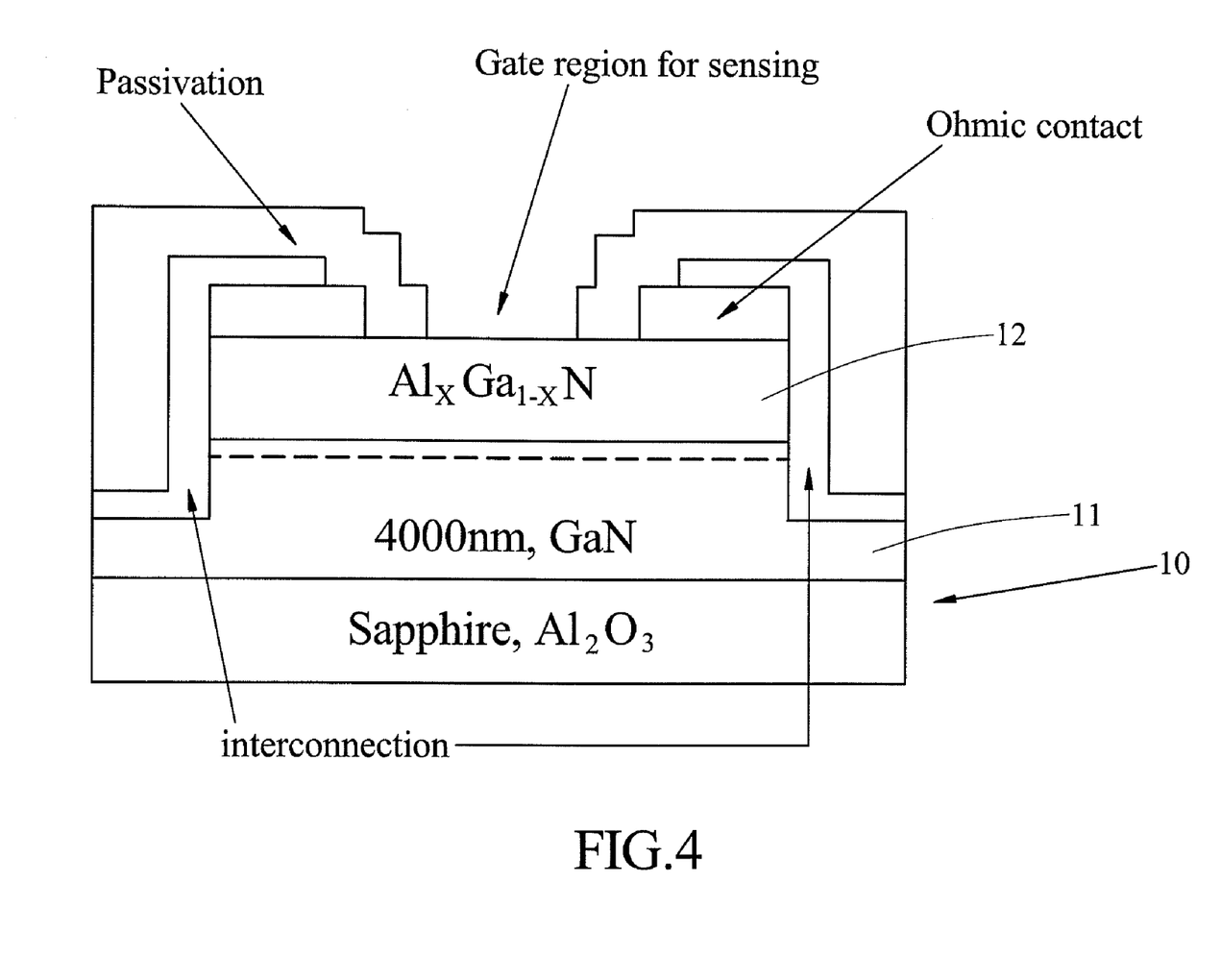
FIG. 4 is a cross-sectional view of a sensing device in accordance with a preferred embodiment of the present invention.
Figure 5:
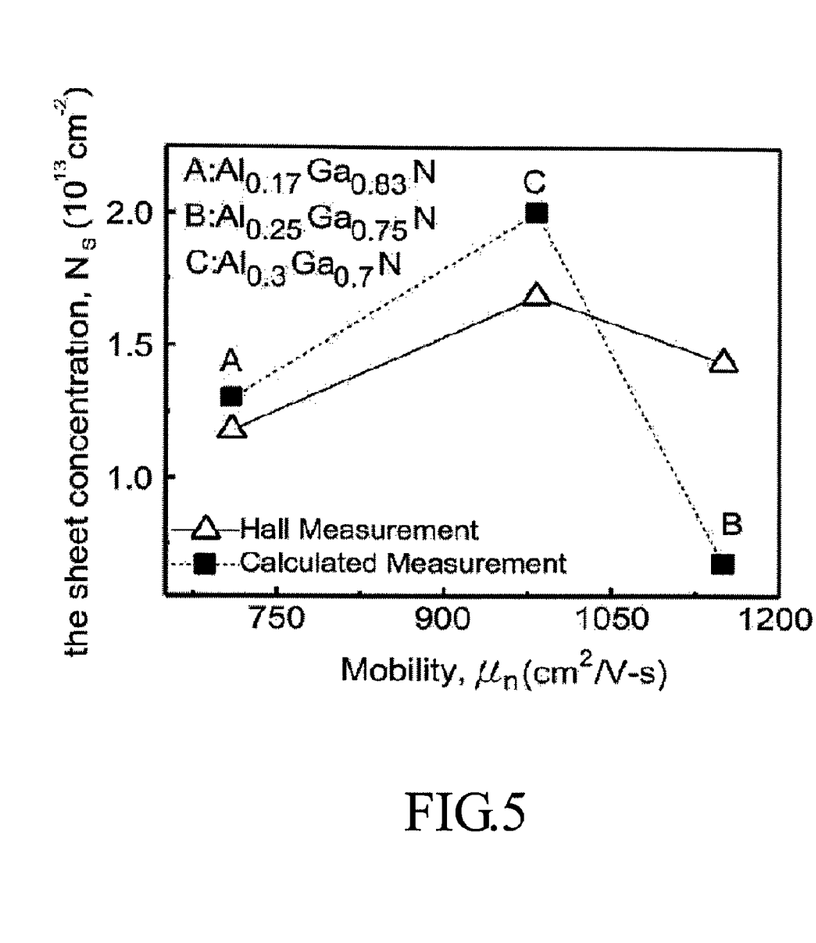
FIG. 5 is a schematic view of carrier mobility and channel carrier concentration of different epitaxial structures in accordance with a preferred embodiment of the present invention.
Figure 6:
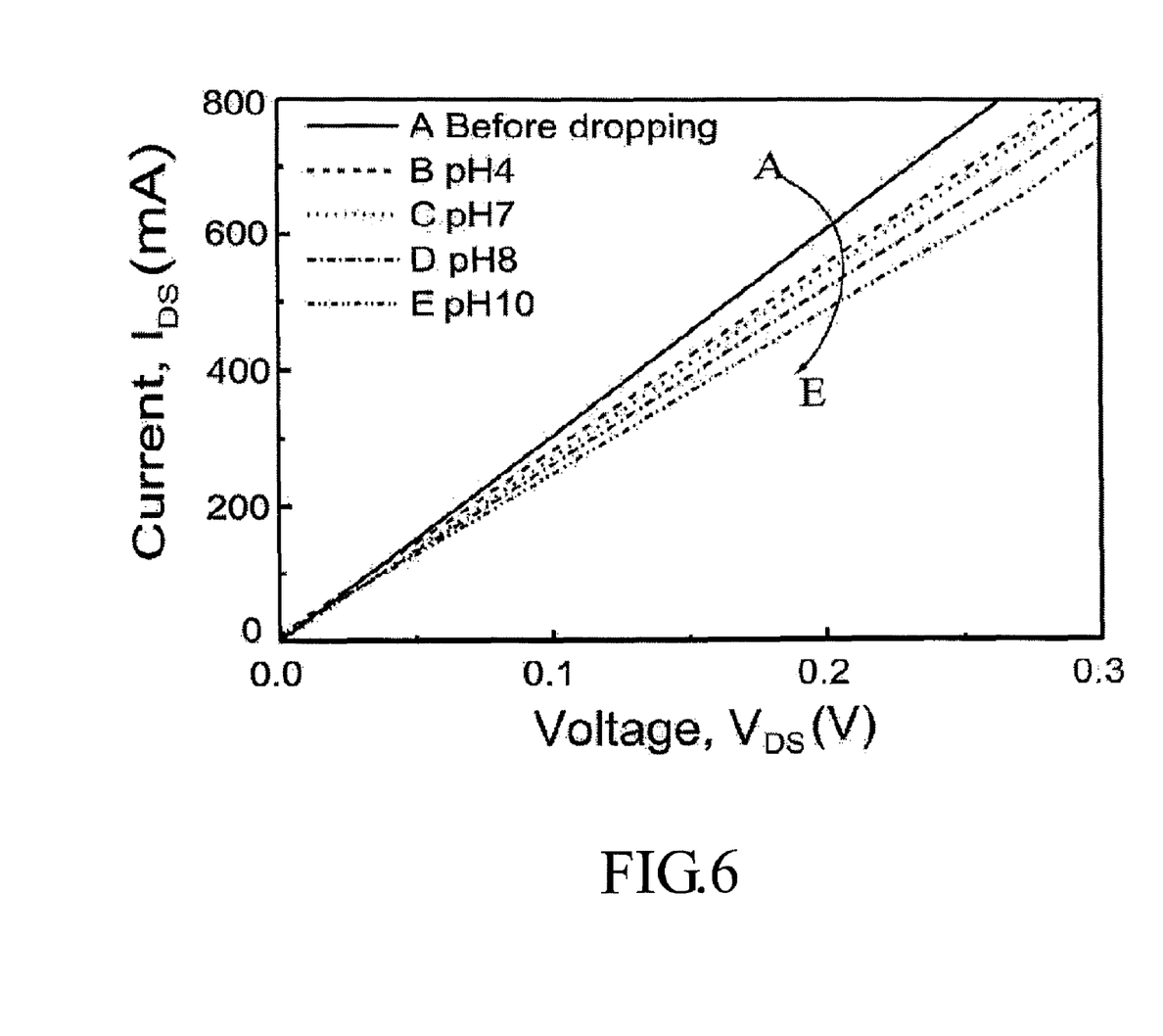
FIG. 6 is a schematic view of a current change of a sensing device at different environments in accordance with a preferred embodiment of the present invention.
Figure 7:
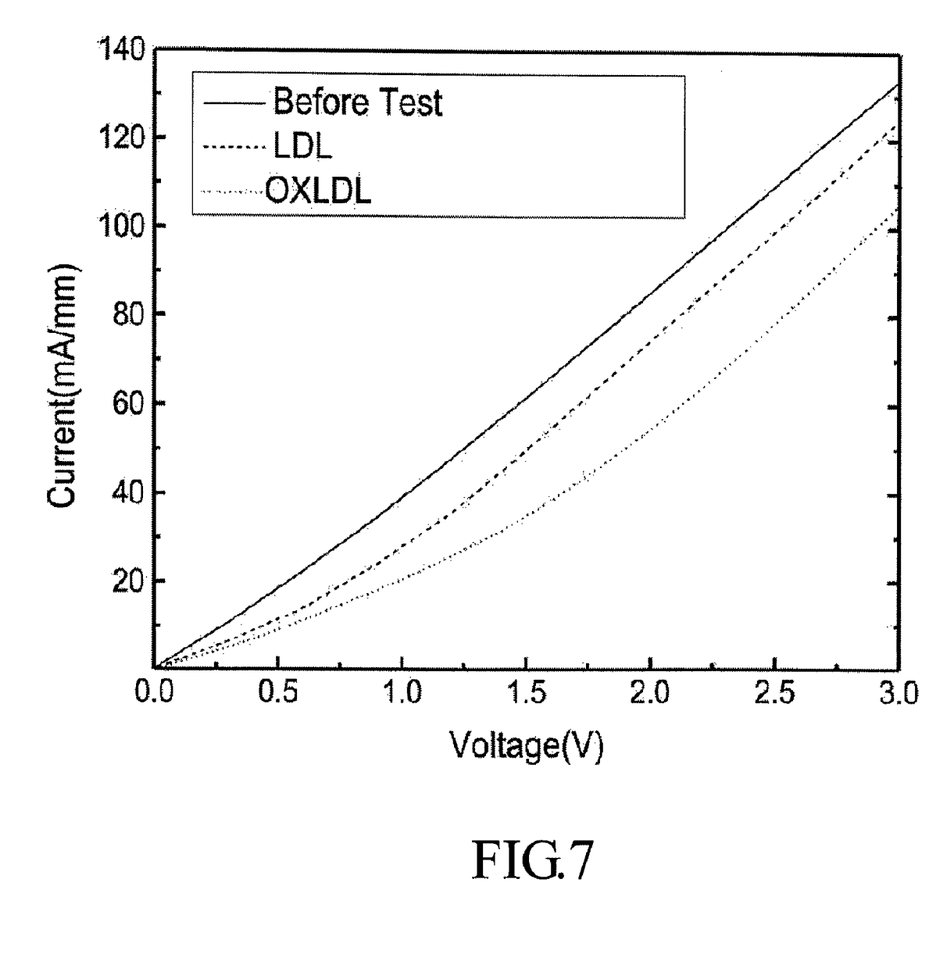
FIG. 7 shows measurement results of natural and oxidized low density lipoproteins in accordance with a preferred embodiment of the present invention.
Figure 8:
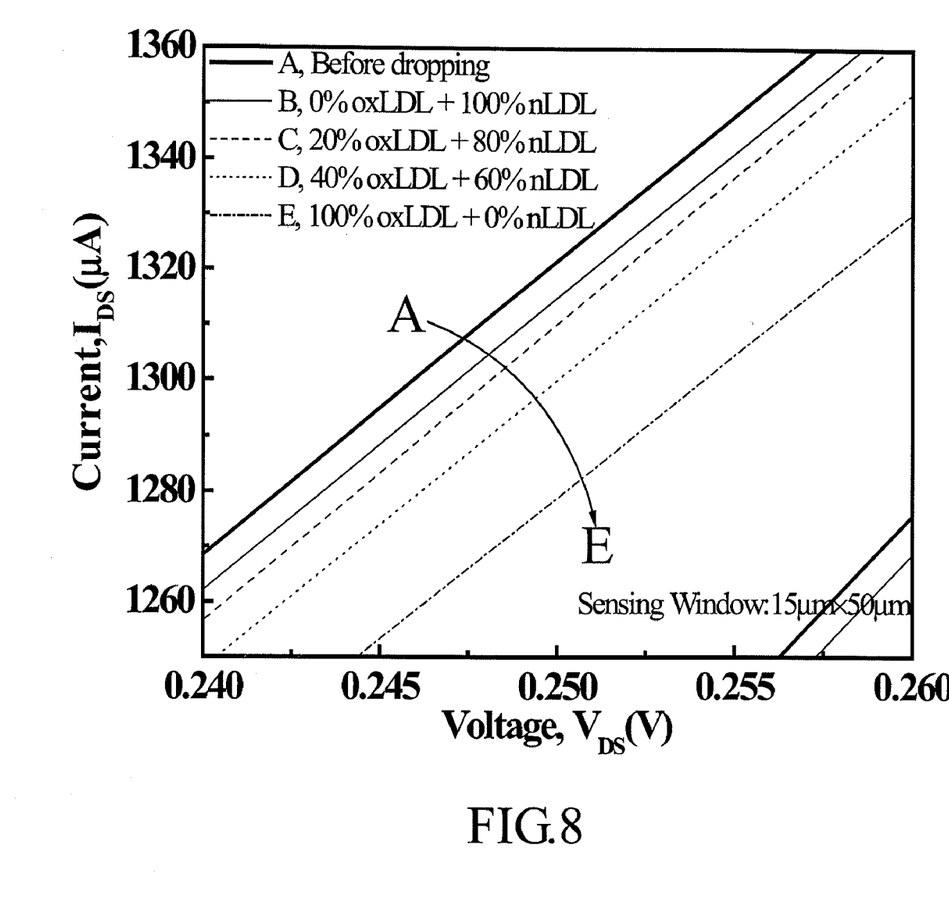
FIG. 8 shows an output current corresponding to different concentrations of an oxidized low density lipoprotein in accordance with a preferred embodiment of the present invention.

The epitaxial wafer structure adopts sapphire as a substrate and is fabricated by a molecular beam epitaxy (MBE) method.

The epitaxial wafer structure adopts sapphire as a substrate and is fabricated by a metalorganic chemical vapor deposition (MOCVD) method.

The aluminum gallium nitride layer 12 of the epitaxial wafer structure comes with an aluminum content with a weight percentage of 17%, and the thickness of the aluminum gallium nitride layer 12 is 45 nm.

The aluminum gallium nitride layer 12 of the epitaxial wafer structure comes with an aluminum content with a weight percentage of 25%, and the thickness of the aluminum gallium nitride layer 12 is 35 nm.

The aluminum gallium nitride layer 12 of the epitaxial wafer structure comes with an aluminum content with a weight percentage of 30%, and the thickness of the aluminum gallium nitride layer 12 is 30 nm.

The source is made of an alloy electrically conductive material which is an ohm-contact alloy material selected from titanium, aluminum, nickel and gold.

The drain is made of an alloy electrically conductive material which is an ohm-contact alloy material selected from titanium, aluminum, nickel and gold The metal connecting wire is made of an electrically conductive material which is an electrically conductive metal material selected from titanium or gold.

The principle of operation and the content of the present invention are described in details as follows. The operating principle of AlGaN/GaN high electron mobility FET produces a two-dimensional electron gas through different AlGaN and GaN Fermi energy levels together with the specific polarization property of the GaN material. As implied in the name, the two-dimensional electron gas moves in a two-dimensional space (which is a plane), but cannot move upward in a direction perpendicular to this plane. For example, the natural world has substances such as graphite which is similar to the two-dimensional electron gas. When the resistance along a graphite plate is measured, it shows that the measured resistance is much smaller than the resistance between two graphite plates. The movement property of the two-dimensional electron gas is clearer than the three-dimensional property, and a cyclonic orbit of the movement is quantized, and electrons are situated at separated energy levels. The two-dimensional electrons can be produced by changing the potential energy at the surface of a semiconductor to form a triangular potential well.

Figure 1:
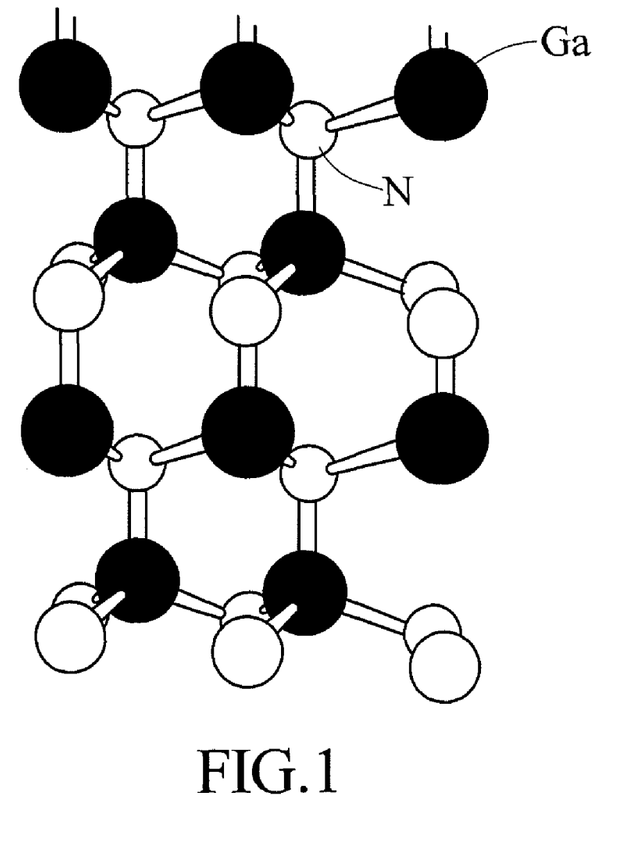
FIG. 1 is a schematic view of GaN molecular structure in accordance with a preferred embodiment of the present invention.
Figure 2A:
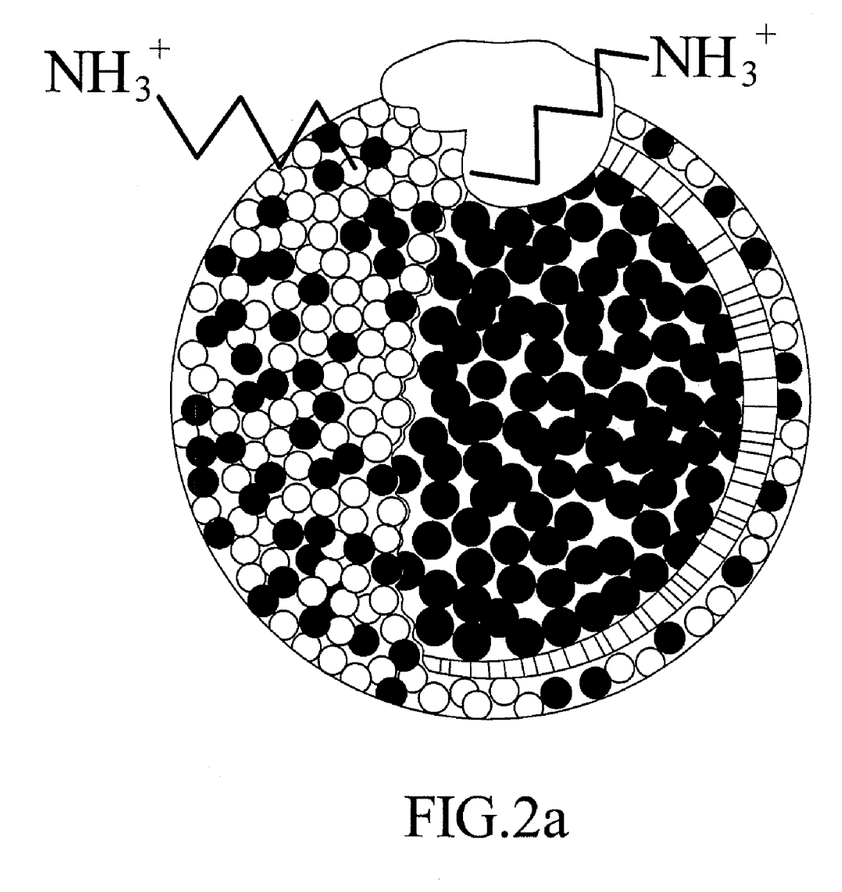
FIG. 2A is a schematic view of super micro molecules of a natural low density lipoprotein in accordance with a preferred embodiment of the present invention.
Figure 2B:
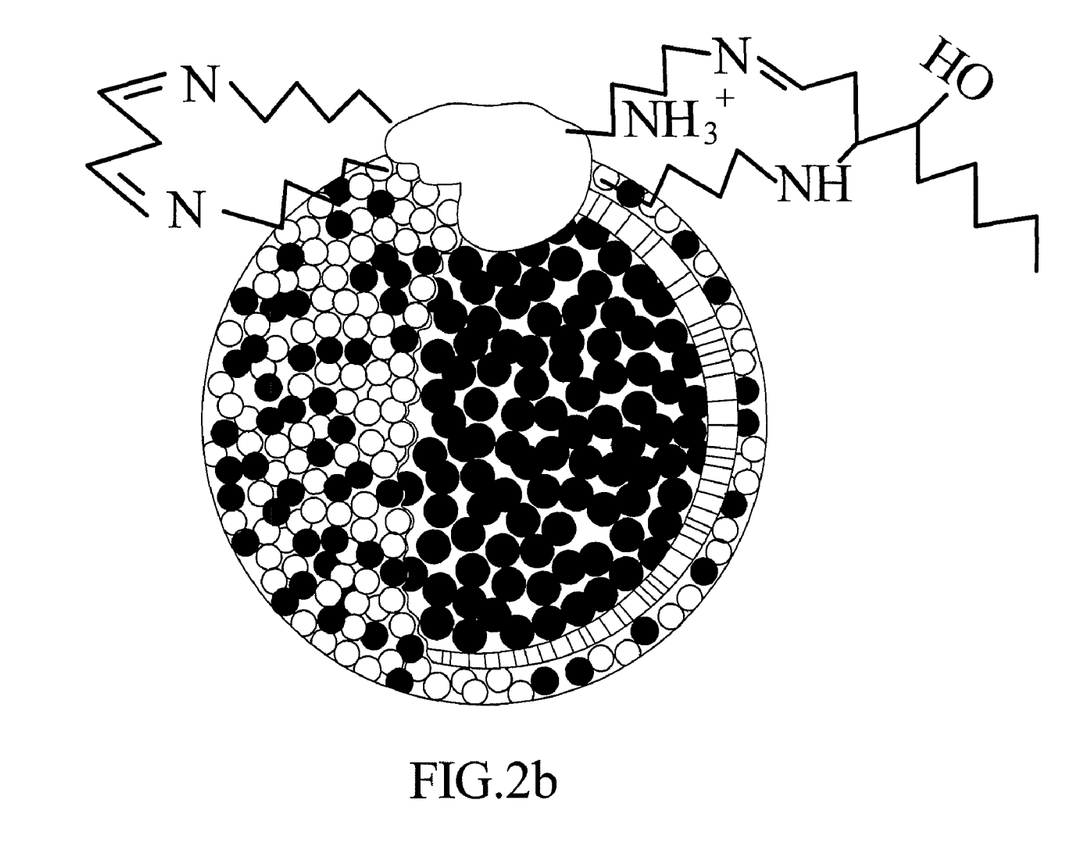
FIG. 2B is a schematic view of super micro molecules of an oxidized low density lipoprotein in accordance with a preferred embodiment of the present invention.
Figure 3:
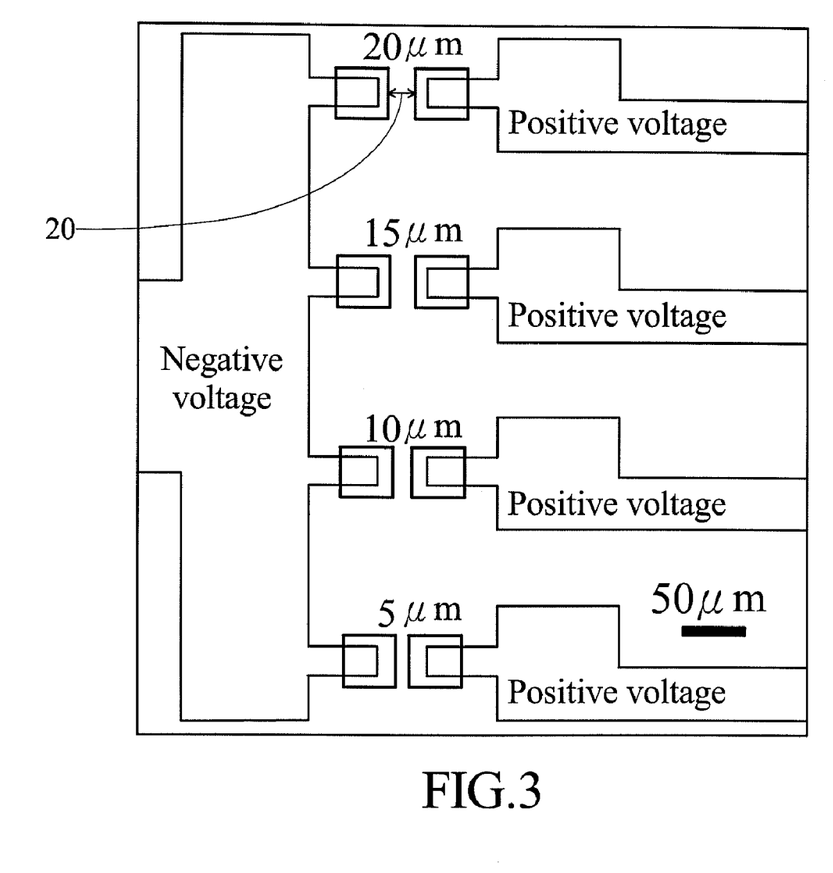
FIG. 3 is a schematic view of a low density lipoprotein sensing device in accordance with a preferred embodiment of the present invention.

The present invention controls atoms by metalorganic chemical vapor deposition (MOCVD) or molecular beam epitaxy (MBE) to deposit layers of electrons onto the epitaxial wafer, and thus an energy gap at a bi-material joint protrudes an energy band suddenly to form the required triangular well. A condition for AlGaN/GaN to form a two-dimensional electron sea mechanism is the polarization effect, in addition to the potential well produced by different energy gap at the heterogeneous joint. GaN is a Wurtzite epitaxy structure which is a perpendicularly asymmetric structure, featuring a greater polarization effect in the vertical direction. The polarization effect is divided into two types, respectively: spontaneous polarization and piezoelectric polarization. A built-in electric field produced by the polarization effect at the AlGaN/GaN heterogeneous joint will form an upward electric field inside AlGaN, such that a negative charge layer is formed on the surface of AlGaN and a positive charge layer is formed on a surface proximate to the AlGaN/GaN interface, and the positive charge layer will induce a high-concentration two-dimensional electron sea in GaN. In other words, a very large current density can be achieved without any doping in AlGaN.

The present invention uses the built-in piezoelectric field produced by the AlGaN/GaN heterogeneous structure to detect the oxidation level of the low density lipoprotein, wherein the natural and oxidized low density lipoprotein detecting solutions adopt NaCl(aq) as a solvent and have a pH value falling in a range of 7~8. At normal temperature and pressure, the cold stored low density lipoprotein is dropped onto the sensing device by a micro tip, and then the electric properties are measured immediately. Preliminary measurements indicate that all ammonia acid radicals ($NH_3^+$) are occurred in the natural low density lipoprotein environment, and the current drop is due to the repulsion of the positive charges on the AlGaN surface by the ammonia acid radical ($NH_3^+$), but the current drops more significantly and the change of current reaches the mA level, since hydroxyl radicals are fully combined with positive charges on the AlGaN surface in the oxidized low density lipoprotein environment and results in a damage of the built-in piezoelectric field.

What is claimed is:

1. An oxidized low density lipoprotein sensing device for a gallium nitride process, which is a gallium nitride high electron mobility transistor (GaN HEMT) device, comprising:
   a gateless AlGaN/GaN sensing transistor device, being an epitaxial wafer structure having a GaN layer and an aluminum gallium nitride layer, and the aluminum gallium nitride layer being disposed on the GaN layer, and the aluminum gallium nitride layer including aluminum of a weight percentage and the aluminum gallium nitride layer having a thickness for achieving a lattice match;
   a testing window, disposed on the epitaxial wafer structure;
   a source, disposed at the epitaxial wafer structure and on a side of the testing window;
   a drain, disposed at the epitaxial wafer structure and on another side of the testing window;
   two metal connecting wires, disposed on the source and the drain respectively, and provided for taking a measurement; and
   a passivation layer, covered onto an external surface of the gateless AlGaN/GaN sensing transistor device except the testing window, for sensing the level of oxidizing proteins in a human body.

2. The oxidized low density lipoprotein sensing device for a gallium nitride process of claim 1, wherein the epitaxial wafer structure has a sapphire substrate and is fabricated by a molecular beam epitaxy (MBE) method.

3. The oxidized low density lipoprotein sensing device for a gallium nitride process of claim 1, wherein the epitaxial wafer structure has a sapphire substrate, and is fabricated by a metalorganic chemical vapor deposition (MOCVD) method.

4. The oxidized low density lipoprotein sensing device for a gallium nitride process of claim 1, wherein the aluminum gallium nitride layer of the epitaxial wafer structure has an aluminum content with a weight percentage of 17%, and a thickness of 45 nm.

5. The oxidized low density lipoprotein sensing device for a gallium nitride process of claim 1, wherein the aluminum gallium nitride layer of the epitaxial wafer structure has an aluminum content with a weight percentage of 25%, and a thickness of 35 nm.

6. The oxidized low density lipoprotein sensing device for a gallium nitride process of claim 1, wherein the aluminum gallium nitride layer of the epitaxial wafer structure has an aluminum content with a weight percentage of 30% and a thickness of 30 nm.

7. The oxidized low density lipoprotein sensing device for a gallium nitride process of claim 1, wherein the source is made of an alloy electrically conductive material which is an ohm-contact alloy material selected from the collection of titanium, aluminum, nickel and gold.

8. The oxidized low density lipoprotein sensing device for a gallium nitride process of claim 1, wherein the drain is made of an alloy electrically conductive material which is an ohm-contact alloy material selected from the collection of titanium, aluminum, nickel and gold.

9. The oxidized low density lipoprotein sensing device for a gallium nitride process of claim 1, wherein the metal connecting wire is made of an electrically conductive material which is an electrically conductive metal material selected from the collection of titanium and gold.

* * * * *